(12) United States Patent
Gemma (10) Patent No.: US 7,204,124 B2
(45) Date of Patent: Apr. 17, 2007

(54) SHEET MATERIAL DETECTING DEVICE

(75) Inventor: Naoyo Gemma, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 104 days.

(21) Appl. No.: 11/000,096

(22) Filed: Dec. 1, 2004

(65) Prior Publication Data

US 2005/0189710 A1 Sep. 1, 2005

(30) Foreign Application Priority Data

Dec. 5, 2003 (JP) ............................. 2003-408275

(51) Int. Cl.
*G01M 7/00* (2006.01)
*G01N 3/30* (2006.01)
*G01N 3/32* (2006.01)
*G01P 15/00* (2006.01)

(52) U.S. Cl. .................................................. 73/12.01
(58) Field of Classification Search ................ 73/12.01
See application file for complete search history.

(56) References Cited

U.S. PATENT DOCUMENTS

| | | | |
|---|---|---|---|
| 5,335,043 A * | 8/1994 | Kluger et al. ................. 399/16 |
| 5,934,140 A * | 8/1999 | Jackson et al. ................ 73/159 |
| 6,097,497 A | 8/2000 | McGraw ..................... 358/1.12 |
| 6,886,263 B2 * | 5/2005 | Chou ........................ 33/27.02 |
| 2003/0053089 A1 * | 3/2003 | Nojiri et al. ................. 358/1.9 |
| 2003/0053090 A1 * | 3/2003 | Nojiri et al. ................. 358/1.9 |

FOREIGN PATENT DOCUMENTS

| | | |
|---|---|---|
| EP | 1286156 A | 2/2003 |
| EP | 1286157 A | 2/2003 |
| WO | WO 03/083711 | 10/2003 |

* cited by examiner

*Primary Examiner*—Michael Cygan
*Assistant Examiner*—Octavia Davis
(74) *Attorney, Agent, or Firm*—Fitzpatrick, Cella, Harper & Scinto (57) ABSTRACT

A sheet material detecting device for identifying the material of a sheet by utilizing an impact applied to the sheet has an impact applying unit which is supported to be rotatable and shiftable toward the sheet, and applies an impact onto the sheet, an impact receiving unit which is supported to be rotatable and shiftable in a state of being in contact with the sheet onto which the impact has been applied, arranged opposite the impact applying unit with a gap permitting the passage of the sheet in-between, and receives via the sheet the impact applied by the impact applying unit onto the sheet, and a signal output unit which outputs a signal in response to the impact applied onto the sheet.

4 Claims, 6 Drawing Sheets

SHEET MATERIAL DETECTING DEVICE

BACKGROUND OF THE INVENTION

1. Field of the Invention

The present invention relates to a signal output device. The invention also relates to a sheet material detecting device, more particularly to a sheet material detecting device which detects the type of a given sheet by applying an impact to the sheet.

2. Related Background Art

Some of the image formation devices which have come into use in recent years, including copying machines, printers and facsimile machines, form images on a wide variety of sheets differing in material, thickness and other attributes, including calendered paper, coated paper and transparent resin film. Any such device, when it is to form an image on any type of these diverse sheets, has to match the operating conditions including the feeding speed and the fixation temperature to the properties of the sheet material, and conventional image formation devices use a sheet material detecting device, integrated with or separately disposed from them, for identifying the sheet material.

Such a sheet material detecting device is disclosed in, for instance, in the U.S. Pat. No. 6,097,497. According to the technique proposed in the patent, the sheet itself is marked in advance with a code consisting of some numeral or symbol and representing information on the sheet, a sensor disposed in a printer reads the code, and the printer uses the code information so read to optimize the printing mode (hereinafter referred to as the marking system). However, such a marking system can be of no use in detecting the material of any uncoded sheet.

Another sheet material detecting device which stops the feeding of a sheet every time it distinguishes the material of the sheet, especially if it is built into a structure such as an image formation device, may affect the performance of the structure.

An object of the present invention is to provide a signal output device, method or the like which can supply information on sheet material even if the sheet is not coded in advance.

Another object of the invention is to provide a sheet material detecting device capable of identifying the material of a sheet while feeding the sheet.

SUMMARY OF THE INVENTION

According to an aspect of the present invention, there is provided a sheet material detecting device for identifying the material of a sheet by utilizing an impact applied to the sheet, comprising:

an impact applying means which is supported to be rotatable and shiftable toward the sheet, and applies an impact onto the sheet, an impact receiving means which is supported to be rotatable and shiftable in a state of being in contact with the sheet onto which the impact has been applied, arranged opposite the impact applying means with a gap permitting the passage of the sheet in-between, and receives via the sheet the impact applied by the impact applying means onto the sheet, and a signal output unit which outputs a signal in response to the impact applied onto the sheet.

The rotatable directions of the impact applying means and of the impact receiving means preferably determine the carrying direction of the sheet. The sheet material detecting device preferably further comprising:

a first supporting means which supports the impact applying means to be rotatable, shiftable toward the sheet and, after the shift, returnable to its original position, and a second supporting means which supports the impact receiving means to be rotatable, shiftable in a state of being in contact with the sheet onto which the impact has been applied and, after the shift, returnable to its original position.

According to another aspect of the present invention, there is provided a sheet material detecting method using an impact applying means, an impact receiving means and a signal output unit, comprising:

an impact applying step at which the impact applying means applies an impact onto the impact receiving means via a sheet, and a signal output step of outputting a signal in response to the impact, and a step of identifying the material of the sheet by comparing the output signal with data stored in advance, wherein:

the impact applying means is supported rotatably and shifts toward the impact receiving means to apply an impact onto the impact receiving means.

According to still another aspect of the present invention, there is provided a sheet material detecting device which applies an impact onto a sheet and identifies the material of the sheet according to the impact transmitted via the sheet, comprising:

an impact applying portion for applying an impact onto the sheet, and an impact receiving portion for receiving the impact transmitted via the sheet and performing detection, wherein:

the impact applying portion and the impact receiving portion oppose each other and regulate the carrying direction of the sheet.

The impact applying portion preferably comprises an impact applying means which shifts toward the sheet and applies impact onto the sheet and a first supporting means which supports the impact applying means to be rotatable, shiftable toward the sheet and, after the shift, returnable to its original position, and the impact receiving portion comprises an impact receiving means which is arranged opposite the impact applying means with a gap permitting the passage of the sheet in-between and shifts in a state of being in contact with the sheet onto which the impact has been applied, and a second supporting means which supports the impact receiving means to be rotatable and shiftable in a state of being in contact with the sheet onto which the impact has been applied and, after the shift, returns it to its original position.

The impact applying means preferably has a spherical or cylindrical shape.

The impact receiving means preferably has a spherical or cylindrical shape.

The first supporting means and the second supporting preferably means use elasticity for returning the impact applying means and the impact receiving means to their respective original positions.

The first supporting means and the second supporting means preferably use pneumatic pressure or hydraulic pressure for returning the impact applying means and the impact receiving means to their respective original positions.

The first supporting means preferably supports the impact applying means via the rotation shaft of the impact applying means and the second supporting means preferably supports the impact receiving means via the rotation shaft of the impact receiving means.

According to a further aspect of the present invention, there is provided a signal output device comprising:

an impact applying means for applying an impact onto a sheet, an impact receiving means which, arranged opposite the impact applying means, receives the impact applied to the impact applying means via the sheet, and a signal output unit which outputs a signal in response to the impact applied onto the sheet, wherein:

the impact applying means has an impact applying portion supported to be rotatable and shiftable toward the sheet.

The present invention can contribute to simplifying the structure and reducing the cost by using the same configuration for the impact applying portion and the impact receiving portion.

DESCRIPTION OF THE PREFERRED EMBODIMENTS

The principle of making it possible to detecting the sheet material by using an impact will be explained below. The impact which an impact receiving portion receives differs with the mechanical characteristics of the sheet material including stiffness, Young's modulus and thickness. Therefore, the type of the sheet material is detected by utilizing these differences. The impact applied to the sheet material is detected by a pressure sensor provided on either the impact applying means side or the impact receiving portion side. Where the pressure sensor is a piezoelectric element such as PZT, the variation of the voltage over time is the signal to be detected. The detected signal is compared with data stored in advance, classified by the type of sheet material, and the type of the fed sheet material is thereby distinguished.

(First Embodiment)

Figure 1:
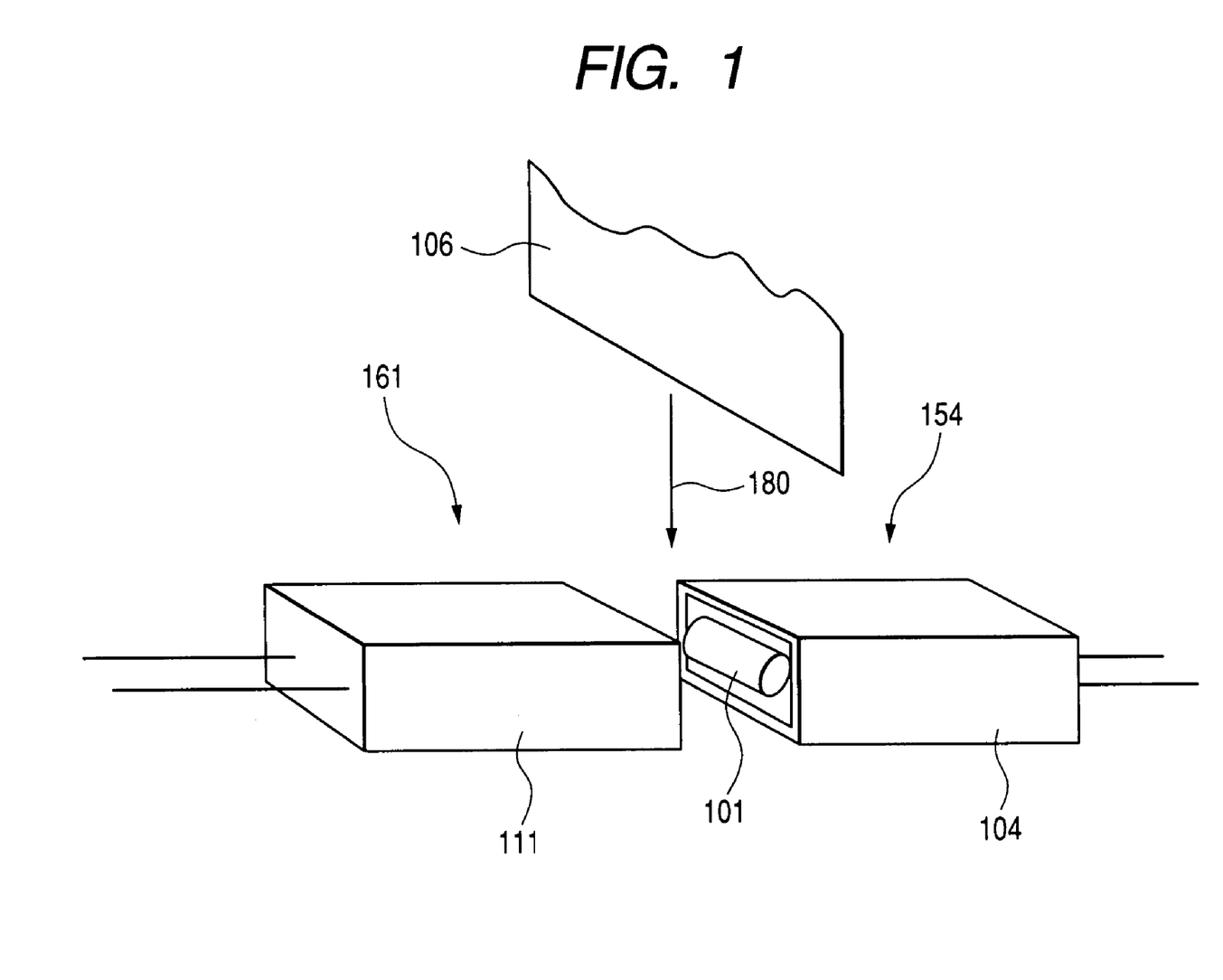
FIG. 1 shows a schematic perspective view of the configuration of a sheet material detecting device, which is a first preferred embodiment of the present invention.

The configuration of a sheet material detecting device, which is a first preferred embodiment of the present invention will be described below with reference to FIG. 1 through FIG. 3. In FIG. 1, reference numeral 154 denotes a impacting unit which is an impact applying portion to give vibration as an impact to a sheet 106, and 161, a impacted unit which is an impact receiving portion for detecting impact energy transmitted via the sheet 106.

Figure 2:
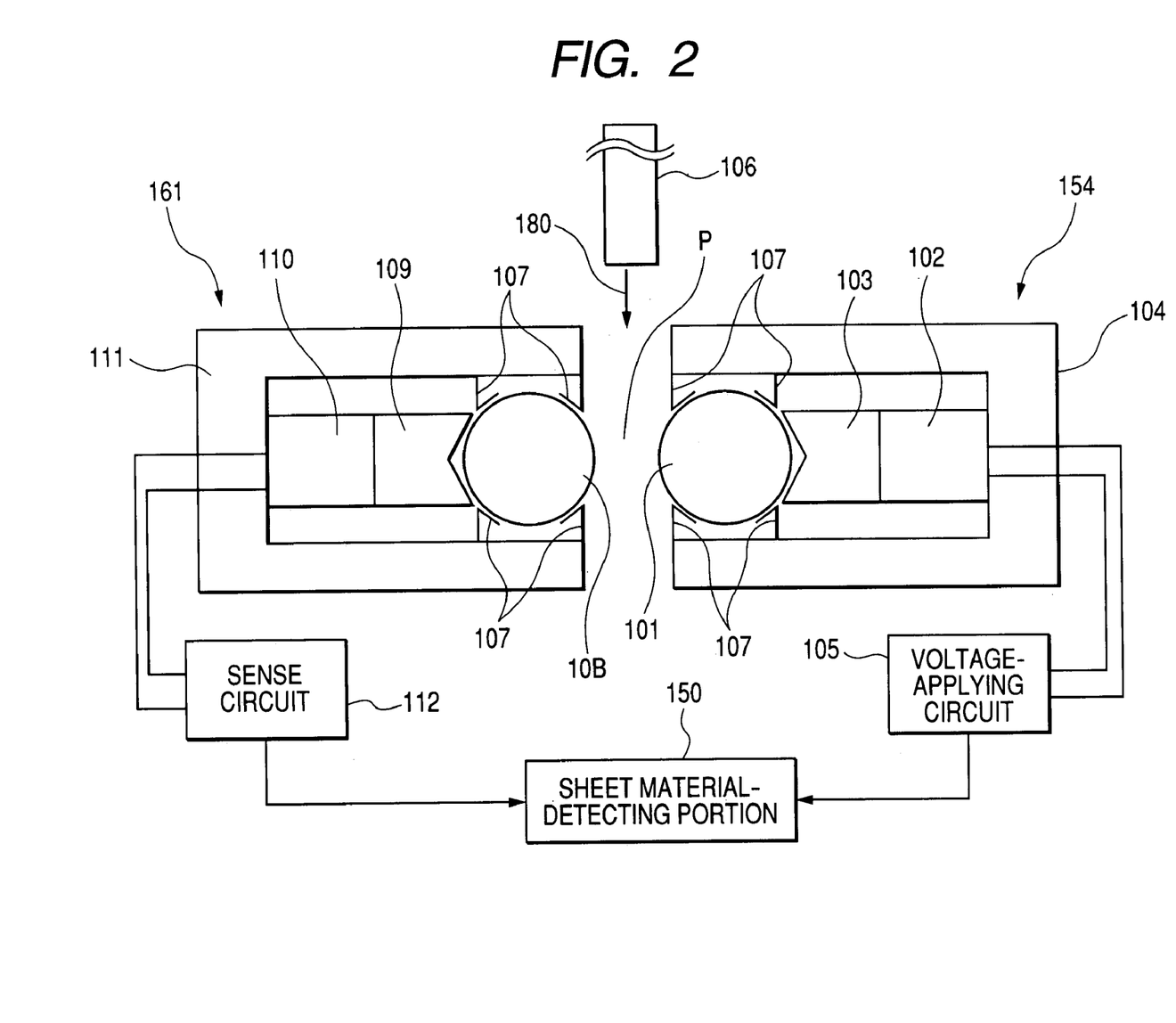
FIG. 2 is a schematic section showing the configuration of the sheet material detecting device.

As shown in FIG. 2, the impacting unit 154 comprises a impacting unit case 104, a impacting member 101 which is impact applying means to vibrate the sheet 106 by giving an impact to the sheet 106, a piezoelectric element 102 which is extended by the application of a voltage from a voltage applying circuit 105, a transmitting member 103 which, disposed between the piezoelectric element 102 and the impacting member 101 and on a side of the piezoelectric element 102 so as to be displaced by an equal distance toward the impacting member by the length of extension of the piezoelectric element, to transmit the extension of the piezoelectric element 102 to the impacting member 101, and a leaf spring group 107 for holding the impacting member 101. A prescribed gap g1 is provided between the impacting member 101 and the transmitting member 103.

The impacted unit 161 comprises a impacted unit case 111, a impacted member 108 which is impact receiving means in contact with the sheet 106 impacted by the application of the impact and subjected to the transmission of the impact of the sheet 106, a piezoelectric element 110 which outputs a voltage signal to a sense circuit 112 by being compressed by the received impact, a transmitting member 109 which, disposed between the impacted member 108 and the piezoelectric element 110 and in a position on the side of the piezoelectric element 110 toward the impacted member 108 to transmit to the piezoelectric element 110 the impact received by the impacted member 108, and another leaf spring group 107 for holding the impacted member 108. A prescribed gap g2 is provided between the impacted member 108 and the transmitting member 109.

The impacted member 108 is so arranged opposite the impacting member 101 so as to form between itself and the impacting member 101 a sheet passage P, consisting of a gap g3, through which the sheet 106 weave either in light contact or not in contact with the members.

A voltage applied by the voltage applying circuit 105 and a signal supplied from the sense circuit 112 according to a voltage signal entered from the impacted piezoelectric element 110 are entered into a sheet material detecting portion 150, and the sheet material detecting portion 150 identifies the type of the sheet on the basis of these signals.

Figure 3:
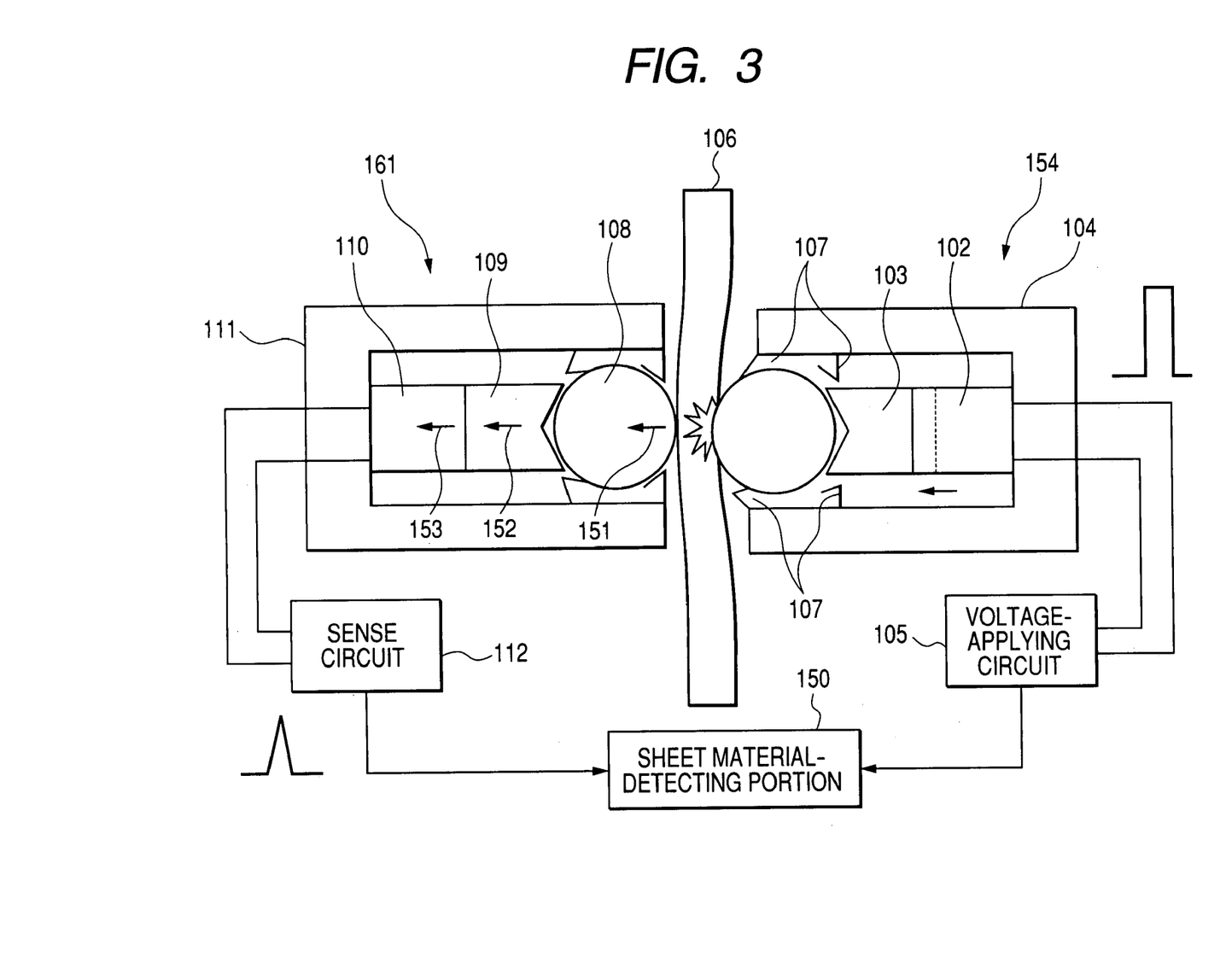
FIG. 3 illustrates the sheet material detecting operation by the sheet material detecting device.

FIG. 3 illustrates the operation to detect the sheet 106 by the sheet material detecting device in this embodiment of the invention. When the sheet 106 is carried to the sheet passage P in the direction of an arrow 180 in FIG. 2, a voltage is applied from the voltage applying circuit 105 to the piezoelectric element of the impacting unit (hereinafter referred to as the impacting piezoelectric element) 102, and the impacting piezoelectric element 102 is extended in the direction of the arrow by the inverse piezoelectric effect according to the level of this voltage. The length of extension of the impacting piezoelectric element at a time per voltage application will be referred to as a "impacting stroke". The displacement of the tip of the element due to this extension is transmitted to the impacting member 101 via the motion of the transmitting member 103, and the impacting member 101 is pushed toward the sheet to collide against the sheet 106. The displacement of the impacting piezoelectric element and of the transmitting member 103 appended thereto toward the impacting member will be hereinafter referred to as the "impacting displacement". This impact is transmitted to the impacted member 108 of the impacted unit in contact with the sheet 106, and the impacted member 108 is thereby moved in the direction of an arrow 151, compressing via the transmitting member 109 in the direction of an arrow 152 the impacted piezoelectric element (hereinafter referred to as the impacted piezoelectric element) 110 in the direction of an arrow 153. The displacement due to the motion of the impacted member 108 toward the impacted piezoelectric element 110 will be hereinafter referred to as the "the impacted displacement". The length of compression to which the impacted piezoelectric element is subjected at a time will be referred to as the "impacted stroke". The compressed impacted piezoelectric element 110 is caused by a piezoelectric effect to generate a voltage signal according to the magnitude of the transmitted impact. The voltage signal is entered into the sense circuit 112.

To add, after the impact ends, the impacting piezoelectric element 102 and the impacted piezoelectric element 110 return to their respective original dimensions, and the impacting member 101 and the impacted member 108 return to their respective original positions.

Figure 4A:
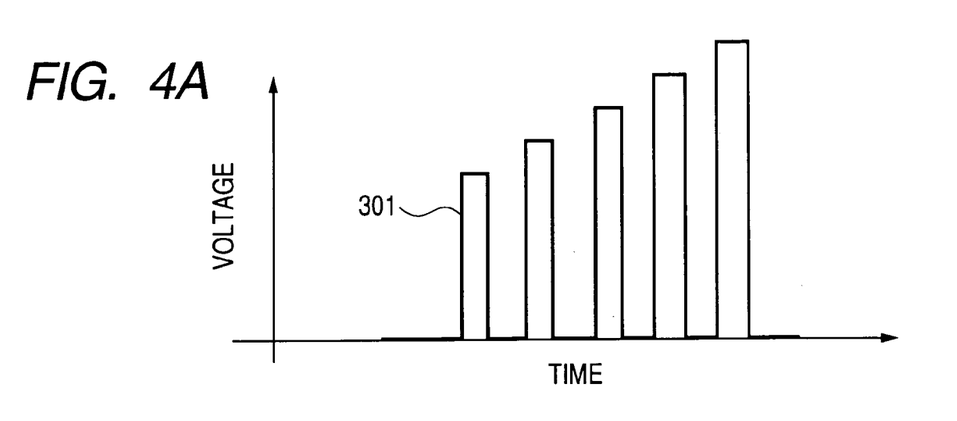
FIGS. 4A, 4B and 4C respectively illustrate the voltage applied, impacting stroke and impacted side output in the sheet material detecting operation by the above sheet material detecting device.
Figure 4B:
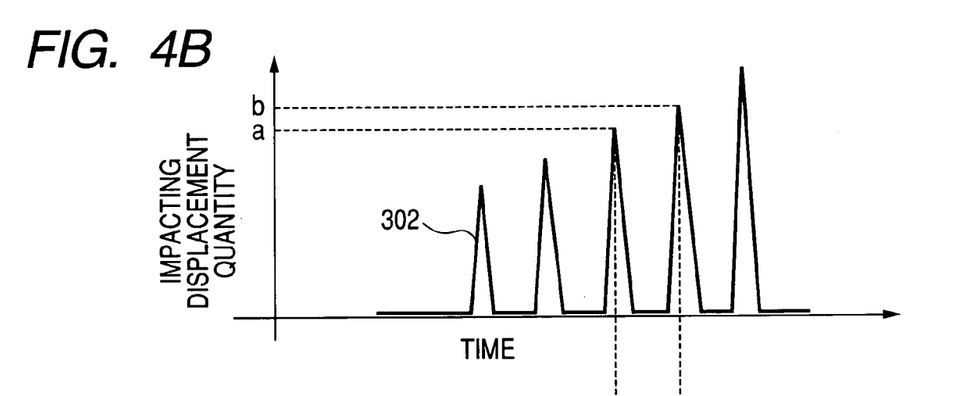

The voltage from the voltage applying circuit 105 is applied a plurality of times at prescribed intervals of time at a successively rising level as shown in FIG. 4A. This voltage application a plurality of times gives rise to a plurality of consecutive impacting strokes. The impacting displacement due to the impacting strokes occurs in a quantity, at time intervals and a number of times matching the level, time intervals and the frequency of applications of the voltage as shown in FIG. 4B. Incidentally, the voltage signal applied by the voltage applying circuit 105 is delivered to the sheet material detecting portion 150 to be used as information for distinguishing the type of sheet material as described earlier.

In order for the impacting displacement in one impacting stroke to generate a impacted stroke via an intervening object, the quantity of the impacting displacement should be greater than the sum of the balance of the subtraction of the thickness of the sheet 106 from the gap g3 between the impacting member 101 and the impacted member 108, the gap g1 between the transmitting member 103 and the impacting member 101, and the gap g2 between the impacted member 108 and the transmitting member 109. Namely the condition expressed in the following formula, where X is the quantity of impacting displacement and T is the sheet thickness, should satisfied:

$$g3-T+g1+g2<X$$

As long as the impacting displacement quantity X fails to satisfy this condition, the impacting displacement is not transmitted to the impacting member 101, and the impacting member is not pushed toward the sheet or, even if the displacement is transmitted and the member is pushed, will not collide against the sheet; or even if it collides, the sheet will not transmit the impact to the impacted member 108; or even if the impact is transmitted and the impacted member 108 a impacted displacement occurs, the impact will not reach the transmitting member 109 and accordingly the impacted piezoelectric element 110 will not be compressed; namely no impacted stroke is generated. As a result, the voltage signal from the impacted piezoelectric element 110 is zero.

Figure 4C:
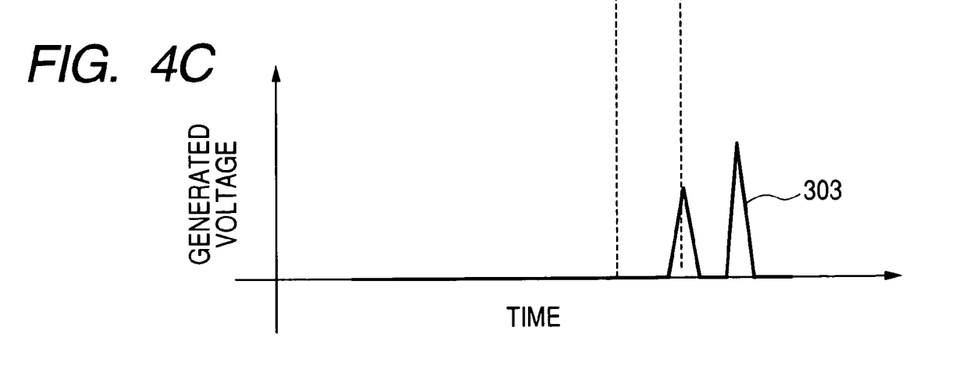

As described above, a series of impacting strokes consists of strokes the impacting displacement quantity X of which successively increases correspondingly to the rise in applied voltage. Therefore, if there is a impacting stroke whose impacting displacement quantity X satisfies the formula above for the first time, every subsequent impacting stroke will satisfy the formula and accordingly gives rise to a impacted stroke. For instance, the impacting stroke whose impacting displacement quantity X is a in FIG. 4B does not satisfy the formula above, but those of b and more in impacting displacement quantity do satisfy it. Therefore, impacted strokes arise matching only the impacting strokes of and after what gives rise to the impacting displacement b, and they cause the impacted piezoelectric element 110 to generate voltages. FIG. 4C shows variations in this voltage shown by the impacted piezoelectric element 110; no impacted stroke is generated matching any impacting stroke whose impacting displacement is less than a, and accordingly the voltage generated then by the impacted piezoelectric element 110 is zero.

A voltage signal outputted from the impacted piezoelectric element 110 is inputted to the sense circuit 112, and a signal corresponding to this voltage signal is outputted from the sense circuit 112. The output signal is inputted to the sheet material detecting portion 150 as described above. The sheet material detecting portion 150 determines the level of the voltage inputted from the voltage applying circuit 105 at which the output from the impacted piezoelectric element 110 begins to be inputted. From the determined level, the thickness T of the sheet 106 is detected. Also from the output of the impacted piezoelectric element 110, the type of the sheet 106 as to material and other attribute can be identified.

Figure 5A:
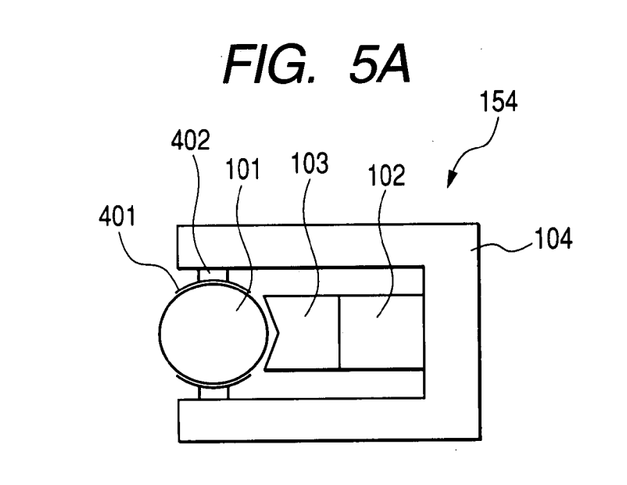
FIGS. 5A, 5B, 5C and 5D illustrate a damper provided in the sheet material detecting device.
Figure 5B:
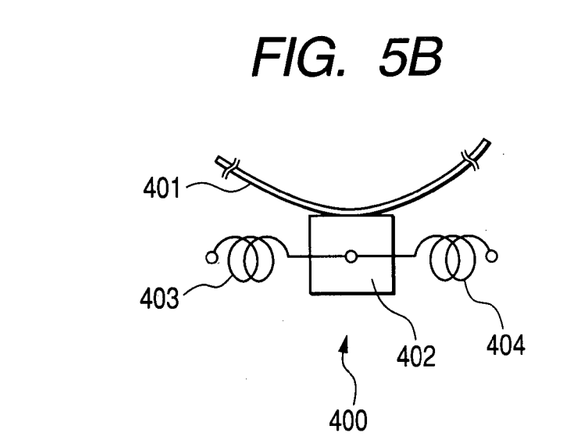
Figure 5C:
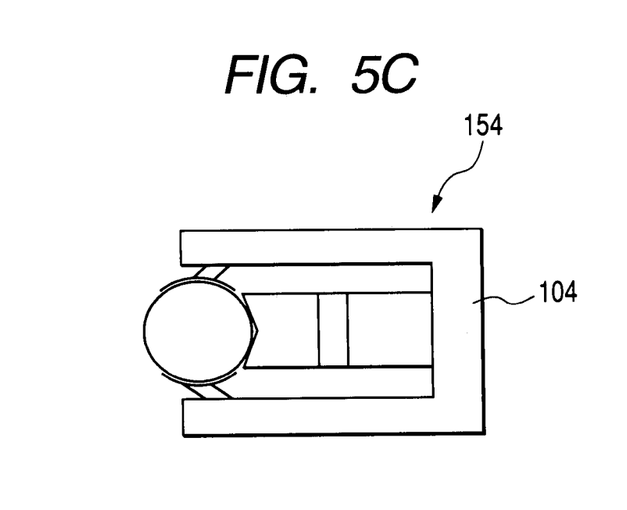

The impacting member 101 has a spherical, cylindrical or wheel-like shape, and has a concave face matching the curved face it is opposed to. It is supported by accepting portions 401 for a damper 400 shown in FIG. 5B, which are first supporting means, to be rotatable in the impacting unit case 104 as shown in FIG. 5A. The damper 400 consists of the accepting portions 401, supports 402 for fixing the accepting portions to the case 104, and two springs 403 and 404 whose two ends are fixed by the supports and the case and disposed opposite each other with the supports between them. The supports 402 and the impacting member 101 held by them before impact are fixed in a position where the tensions of the two springs are balanced with each other as shown in FIG. 5B.

Figure 5D:
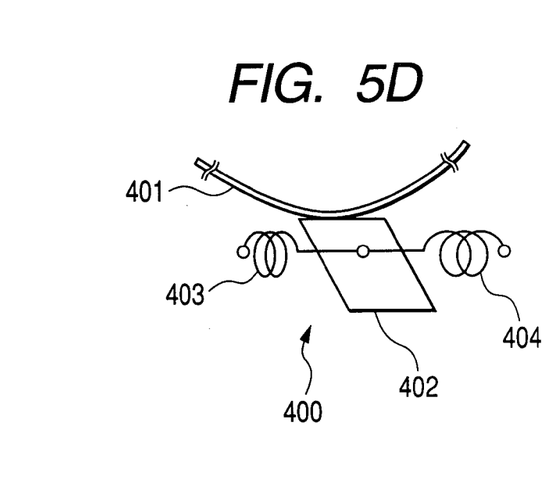

When impact is applied, as the impacting piezoelectric element 102 extends to push out the impacting member 101, the supports 402 compress the spring 403 toward the impacted unit 161 as shown in FIG. 5D and, while extending the spring 404 positioned toward the impacting piezoelectric element 102, are deformed as shown in FIGS. 5A and 5D. When the impacting piezoelectric element 102 contracts to its original dimensions after the impact is over, the extension of the spring 403 and the contraction of the spring 404 return the supports 402 to their original positions, and along with that the impacting member 101 also returns to its original position.

The impacted member 108 also has a spherical, cylindrical or wheel-like shape, and held by accepting portions of a damper of the same structure as the damper 400, which is second supporting means, to be rotatable, shiftable and returnable to its original position within the impacted unit case 111.

Not only does the configuration described above contribute to simplification but also, the moment at which an impact is applied to the sheet 106 in the gap g3, the two members function as rollers to facilitate the movement of the sheet. For this reason, even while the sheet 106 is being carried, the type of the sheet can be identified without having to stop its motion. Thus, it is made possible to optimize the imaging process according to the type of the sheet 106 while adapting to a faster speed, resulting in higher image quality and power saving. Furthermore, the use of the same configuration for the principal parts of the impacting unit 154 and the impacted unit 161 as described above makes possible simplification of the structure and a reduction in cost. The configuration also helps broaden the choice of the installation space and facilitates high-speed paper feeding, because there is no obstruction to paper feeding.

(Second Embodiment)

Figure 6A:
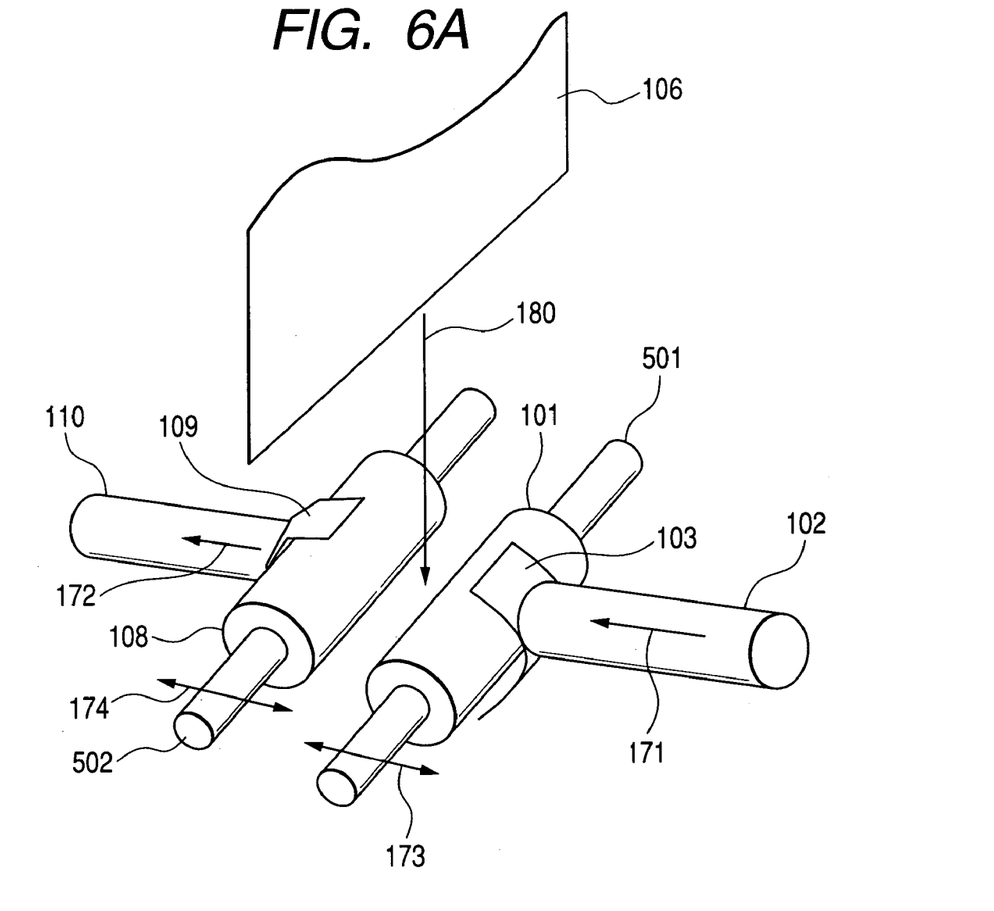
FIGS. 6A and 6B show a perspective view of the essential part of a sheet material detecting device, which is a second preferred embodiment of the invention.

FIG. 6A shows a perspective view of the essential part of a sheet material detecting device, which is a second preferred embodiment of the present invention. In FIG. 6A, the same reference signs as in FIG. 2 denote respectively the same or equivalent constituent parts.

Figure 6B:
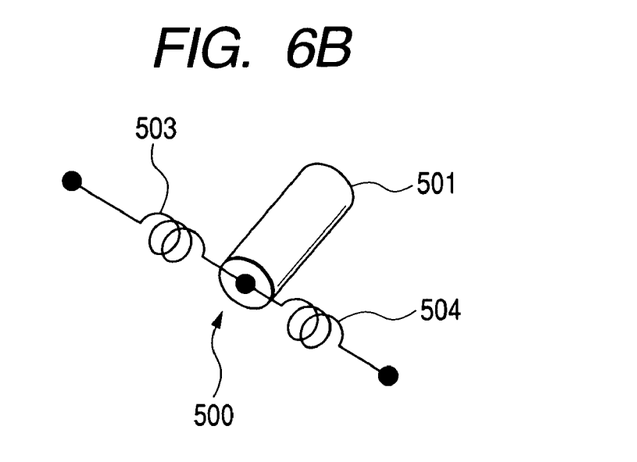

In FIGS. 6A and 6B, reference numeral 501 denotes the rotation shaft of the cylindrically shaped impacting member 101, and the rotation shaft 501 is provided with two springs 503 and 504 constituting part of a damper 500, which is first supporting means, in the moving direction of the impacting member 101 and disposed opposite each other as shown in FIG. 6B. The rotation shaft 501 before impact is fixed in a position where the tensions of the two springs are balanced with each other.

When impact is applied, as the impacting piezoelectric element 102 extends in the direction of the arrow 171 to push out the impacting member 101, along with that the spring 503 toward the impacted piezoelectric element is compressed and the spring 504 positioned toward the impacting piezoelectric element 102 is extended. When the impacting piezoelectric element 102 contracts to its original dimensions after the impact is over, the compressed spring 503 is extended and the extended spring 504 contracts to return to their original positions, and along with that the impacting member 101 also returns to its original position. Though not shown, the impacted member 108 is also held via a rotation shaft 502 by a damper of a similar configuration to the damper 500, which is second supporting means, to be shiftable in the direction of an arrow 172 toward the impacted piezoelectric element and to be returnable to its original position. The directions of the shifting and returning of the impacting member 101 and the impacted member 108 are indicated by arrows 173 and 174, respectively, in FIG. 6A.

In this embodiment, the impacting member 101 and the impacted member 108 can rotate around the rotation shafts 501 and 502. In this structure, even the moment at which an impact is applied to the sheet 106 in the gap g3, the two members function as rollers to facilitate the movement of the sheet. For this reason, even while the sheet 106 is being carried, the type of the sheet can be identified without having to stop its motion.

Although the examples of springs shown in FIGS. 5B, 5D and 6B are coil springs in the first and second embodiments, the usable means of damping according to the invention are not limited to them, but pneumatic or hydraulic dampers can be used instead.

(Third Embodiment)

A method of detection according to the present invention will be described with reference to FIG. 1, wherein reference numeral 154 denotes an impact applying portion; 101, rotatably supported impact applying means; 106, a sheet; and 161, an impact receiving portion.

The sheet 106 is a sheet that can be carried within a copying machine or any other image formation device, such as usual copying paper (plain paper), calendered paper, coated paper or a transparent resin film. Detection of a sheet material in the context of the invention includes not only the identification of the sheet material but also, for instance, discrimination of sheets of the same material merely by the thickness.

First, the rotatably supported impact applying means 101 shifts toward the sheet 106 and the impact receiving portion 161 carried along the sheet passage P in the direction of the arrow 180. Then, the impact applying means applies an impact to the impact receiving means via the sheet. The impact applying means, though coming into contact with the sheet when applying the impact, immediately retracts to go out of contact with the sheet once it has applied the impact. As the impact applying means is held in a rotatable state, it can apply an impact on a sheet being carried, i.e. a sheet in a moving state, without obstructing the motion of the sheet. Naturally, the wear of the impact applying means due to contact with the sheet at the time of applying the impact can be restrained.

It is preferable to hold not only the impact applying means but also the impact receiving means rotatably. The impact can be applied by striking the member against the sheet, but the member continuously vibrating in prescribed cycles can as well be pressed against the impact receiving portion via the sheet.

It is also conceivable to compose the signal output device of the impact applying means, the impact receiving means and a signal output unit, and to perform discrimination using a signal from the signal output device separately. For instance, discrimination can be accomplished with a computer externally connected to a copying machine. In another preferable configuration, unnecessary noise and other elements can be removed by using data from the signal output unit in which the impact applying portion and the impact receiving portion are in direct contact with each other with no intervening presence of a sheet.

This application claims priority from Japanese Patent Application No. 2003-408275 filed Dec. 5, 2003, which is hereby incorporated by reference herein.

What is claimed is:

1. A sheet material detecting device for identifying the material of a sheet by utilizing an impact applied to the sheet, comprising:

an impact applying means which is supported to be rotatable and shiftable toward the sheet, for applying an impact onto the sheet, said impact applying means comprising an impacting member and a first transmitting member with a gap provided between the impacting member and the first transmitting member, an impact receiving means which is supported to be rotatable and shiftable in a state of being in contact with the sheet onto which the impact has been applied, arranged opposite the impact applying means with a gap permitting the passage of said sheet in-between, and receives via the sheet the impact applied by the impact applying means onto the sheet, and a signal output unit which outputs a signal in response to the impact applied onto the sheet.

2. A sheet material detecting method using an impact applying means, an impact receiving means and a signal output unit, comprising:

an impact applying step at which said impact applying means applies an impact onto said impact receiving means via a sheet, said impact applying means comprising an impacting member and a first transmitting member with a gap provided between the impacting member and the first transmitting member, a signal output step of outputting a signal in response to said impact, and a step of identifying the material of the sheet by comparing the output signal with data stored in advance, wherein:

said impact applying means is supported rotatably and shifts toward said impact receiving means to apply an impact onto said impact receiving means.

3. A signal output device comprising:

an impact applying means for applying an impact onto a sheet, said impact applying means comprising an impacting member and a first transmitting member with a gap provided between the impacting member and the first transmitting member, an impact receiving means which, arranged opposite the impact applying means, receives the impact applied to the impact applying means via the sheet, and a signal output unit which outputs a signal in response to the impact applied onto the sheet, wherein:

said impact applying means has an impact applying portion supported to be rotatable and shiftable toward the sheet.

4. A sheet material detecting device according to claim 1, wherein said impact receiving means is supported to be rotatable and comprises an impacted member and a second transmitting member and a formula of (1) is satisfied:

$$g3 - T + g1 + g2 < X \qquad (1)$$

wherein X is the quantity of impacting displacement; T is the sheet thickness; g1 is a gap between the impacting member and the first transmitting member; g2 is a gap between the impacted member and the second transmitting member; and g3 is a gap between the impacting member and the impacted member.

* * * * *

UNITED STATES PATENT AND TRADEMARK OFFICE
CERTIFICATE OF CORRECTION

PATENT NO. : 7,204,124 B2  Page 1 of 1
APPLICATION NO. : 11/000096
DATED : April 17, 2007
INVENTOR(S) : Naoyo Gemma It is certified that error appears in the above-identified patent and that said Letters Patent is hereby corrected as shown below:

COLUMN 2:
Line 58, "preferably means" should read --means preferably--.

COLUMN 5:
Line 39, "satisfied:" should read --satisfy:--.
Line 50, "108 a" should read --108 to an--.

Signed and Sealed this

Fourth Day of March, 2008

JON W. DUDAS
*Director of the United States Patent and Trademark Office*